(12) United States Patent
English et al.

(10) Patent No.: US 12,053,637 B2
(45) Date of Patent: Aug. 6, 2024

(54) PREFORMED WIRE ROUTES

(71) Applicant: Cardiac Pacemakers, Inc., St. Paul, MN (US)

(72) Inventors: James Michael English, Cahir (IE); Moira B. Sweeney, St. Paul, MN (US); Robert Allen Jones, Lake Elmo, MN (US); Benjamin J. Haasl, Forest Lake, MN (US); Trey Henry Achterhoff, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 17/408,931

(22) Filed: Aug. 23, 2021

(65) Prior Publication Data

US 2022/0062648 A1 Mar. 3, 2022

Related U.S. Application Data

(60) Provisional application No. 63/072,371, filed on Aug. 31, 2020.

(51) Int. Cl.
*A61N 1/375* (2006.01)
(52) U.S. Cl.
CPC ........ *A61N 1/3754* (2013.01); *A61N 1/37512* (2017.08)
(58) Field of Classification Search
None
See application file for complete search history.

(56) References Cited

U.S. PATENT DOCUMENTS 5,420,656 A * 5/1995 Kohmoto ................. G02B 7/20
359/813
5,535,097 A * 7/1996 Ruben .................. A61N 1/3752
361/728

(Continued)

FOREIGN PATENT DOCUMENTS

CN 115885433 A 3/2023
GB 2124495 A * 2/1984 ........... A61N 1/3754

(Continued)

OTHER PUBLICATIONS

"International Application Serial No. PCT/US2021/047088, International Search Report mailed Nov. 30, 2021", 4 pgs.

(Continued)

*Primary Examiner* — Erica S Lee
(74) *Attorney, Agent, or Firm* — Schwegman Lundberg & Woessner, P.A.

(57) ABSTRACT

Systems and methods to couple electrical contacts of a header of a medical device to respective feedthrough pins of a connector block of a medical device housing using a preformed wire are disclosed. The preformed wire can include a proximate portion comprising a number of turns shaped to engage a feedthrough pin. The number of turns of the preformed wire, once engaged with the feedthrough pin, can physically separate a major portion of the preformed wire from the connector block and the housing. The major portion of the preformed wire can be shaped to route a distal portion of the preformed wire to a first electrical contact of the header when the proximate portion of the preformed wire engages the feedthrough pin.

16 Claims, 6 Drawing Sheets

(56) References Cited

U.S. PATENT DOCUMENTS

| | | | |
|---|---|---|---|
| 8,162,684 B1* | 4/2012 | Sochor | H01R 13/639 439/289 |
| 2006/0110962 A1* | 5/2006 | Powell | H01R 11/22 439/169 |
| 2009/0118784 A1* | 5/2009 | Alexander | A61N 1/3752 607/36 |
| 2013/0285777 A1* | 10/2013 | Piascik | H01F 41/10 29/605 |
| 2014/0075752 A1 | 3/2014 | Swanson et al. | |
| 2014/0141661 A1* | 5/2014 | Veigel | H01R 13/114 439/884 |
| 2017/0143979 A1* | 5/2017 | Kane | A61N 1/375 |
| 2018/0169419 A1* | 6/2018 | Baade | A61N 1/3754 |
| 2019/0168005 A1 | 6/2019 | Li et al. | |
| 2020/0287398 A1* | 9/2020 | Delose | B25F 5/00 |
| 2020/0324122 A1* | 10/2020 | Villavicencio | A61N 1/37512 |

FOREIGN PATENT DOCUMENTS

| | | |
|---|---|---|
| WO | WO-2019082032 A1 | 5/2019 |
| WO | WO-2022046604 A1 | 3/2022 |

OTHER PUBLICATIONS

"International Application Serial No. PCT/US2021/047088, Written Opinion mailed Nov. 30, 2021", 6 pgs.

"International Application Serial No. PCT/US2021/047088, International Preliminary Report on Patentability mailed Mar. 9, 2023", 8 pgs.

"European Application Serial No. 21770370.1, Response Filed Sep. 27, 2023 to Communication pursuant to Rules 161(1) and 162 EPC mailed Apr. 11, 2023", 9 pgs.

* cited by examiner

PREFORMED WIRE ROUTES

CLAIM OF PRIORITY

This application claims the benefit of priority under 35 U.S.C. § 119(e) of U.S. Provisional Patent Application Ser. No. 63/072,371, filed on Aug. 31, 2020, which is herein incorporated by reference in its entirety.

TECHNICAL FIELD

This document relates generally to electrical connection of components in a medical device, and more particularly, but not by way of limitation, to systems and methods for coupling a preformed wire between a housing of an implantable medical device and an electrical contact in a header coupled to the housing.

BACKGROUND

Medical devices can be implanted or implantable in a body of a patient, such as to monitor patients, including detecting or sensing physiologic information from the patient, such as one or more of heart sounds, respiration (e.g., respiratory rate (RR), tidal volume (TV), etc.), impedance (e.g., thoracic impedance, cardiac impedance, cutaneous impedance, etc.), pressure (e.g., blood pressure), cardiac activity (e.g., heart rate, cardiac electrical information, etc.), chemical (e.g., electrolyte), physical activity, posture, plethysmography, or one or more other physiologic information of the patient, and, in certain examples, provide therapy to the patient in clinical and ambulatory settings. Implantable medical devices (IMDs) can include cardiac rhythm management (CRM) devices, such as pacemakers, cardiac resynchronization devices, cardioverters, defibrillators, drug delivery devices, or one or more other IMDs implanted or implantable within a body of, or subcutaneously to, a patient.

IMDs often include a hermetically sealed housing containing electronic circuitry of the IMD (e.g., one or more signal processing or control circuits, telemetry circuits, therapy circuits, power management circuits, etc.) and a power source, and one or more lead ports in a header outside of the hermetically sealed housing to couple one or more leads having one or more electrodes or other sensors positioned at various locations in or near a heart of the patient, such as in one or more of the atria or ventricles, to the IMD. Separate from, or in addition to, the one or more electrodes or other sensors of the leads, the IMD can include one or more electrodes or other sensors (e.g., a pressure sensor, an accelerometer, a gyroscope, a microphone, etc.) powered by a power source in the IMD. The one or more electrodes or other sensors of the leads, the IMD, or a combination thereof, can be configured detect physiologic information from the patient, or provide one or more therapies or stimulation to the patient.

Lead ports include electrical contacts for communicating electrical signals into and out of the IMD, such as between the electronic circuitry of the IMD and one or more electrodes coupled to the one or more leads. The present inventors have recognized, among other things, a need to reduce the cost and complexity of electrical connection of one or more electrical contacts of the one or more lead ports to respective electronic circuitry inside the hermetically sealed housing.

SUMMARY

Systems and methods to couple electrical contacts of a header of a medical device to respective feedthrough pins of a connector block of a medical device housing using a preformed wire are disclosed. The preformed wire can include a proximate portion comprising a number of turns shaped to engage a feedthrough pin. The number of turns of the preformed wire, once engaged with the feedthrough pin, can physically separate a major portion of the preformed wire from the connector block and the housing. The major portion of the preformed wire can be shaped to route a distal portion of the preformed wire to a first electrical contact of the header when the proximate portion of the preformed wire engages the feedthrough pin.

In certain examples, the number of turns of the proximate portion of the preformed wire can form a lumen configured to engage the feedthrough pin, such as prior to attachment via weld (e.g., resistance welded, laser welded, spot welded, etc.). The feedthrough pin can be shaped to retain the proximate end of the preformed wire. Spacing between successive turns of the proximate end of the preformed wire can provide variance of one or more diameters of the number of turns when compressed, such as when placed and pressed onto the feedthrough pin.

An example (e.g., "Example 1") of subject matter (e.g., a system) may comprise a medical device including a housing comprising a first connector block, the first connector block comprising a first feedthrough pin, a header comprising a lead port having a first electrical contact, and a first preformed wire having a proximate portion comprising a number of turns shaped to engage the first feedthrough pin, the number of turns configured to physically separate a major portion of the first preformed wire from the first connector block and the housing when the proximate portion of the first preformed wire engages the first feedthrough pin, and the major portion of the first preformed wire shaped to route a distal portion of the first preformed wire to the first electrical contact of the header when the proximate portion of the first preformed wire engages the first feedthrough pin.

In Example 2, the subject matter of Example 1 may optionally be configured such that the first preformed wire is configured to electrically couple the first feedthrough pin to the first electrical contact when the proximate portion of the first preformed wire engages the first feedthrough pin and the distal portion of the first preformed wire engages the first electrical contact.

In Example 3, the subject matter of any one or more of Examples 1-2 may optionally be configured such that the number of turns includes two or more turns.

In Example 4, the subject matter of any one or more of Examples 1-3 may optionally be configured such that the number of turns is between two and four turns and the first feedthrough pin has a length commensurate with the number of turns and a diameter of the preformed wire.

In Example 5, the subject matter of any one or more of Examples 1-4 may optionally be configured such that the number of turns form a lumen configured to engage the first feedthrough pin.

In Example 6, the subject matter of any one or more of Examples 1-5 may optionally be configured such that the first feedthrough pin is shaped to retain the lumen of the proximate end of the first preformed wire once placed over and pressed onto the first feedthrough pin.

In Example 7, the subject matter of any one or more of Examples 1-6 may optionally be configured such that the first feedthrough pin includes engaging means configured to retain the proximate end of the first preformed wire once the lumen is inserted over and pressed onto the first feedthrough pin.

In Example 8, the subject matter of any one or more of Examples 1-7 may optionally be configured such that the number of turns comprises at least two turns having different diameters, forming a tapered lumen.

In Example 9, the subject matter of any one or more of Examples 1-8 may optionally be configured such that the number of turns comprises a top turn adjacent the major portion of the first preformed wire having a diameter smaller than a bottom turn adjacent a proximate end of the proximate portion of the first preformed wire.

In Example 10, the subject matter of any one or more of Examples 1-9 may optionally be configured such that the number of turns are positioned to include a spacing between at least two successive turns of the number of turns, the spacing configured to provide variance of a diameter of at least one of the number of turns when compressed.

In Example 11, the subject matter of any one or more of Examples 1-10 may optionally be configured such that the first preformed wire includes an alloy wire having a coating that contrasts a physical appearance of the alloy wire to aid in visual inspection of the first preformed wire and the coating includes at least one of a colored or UV fluorescence coating.

In Example 12, the subject matter of any one or more of Examples 1-11 may optionally be configured such that the first connector block comprises a plurality of feedthrough pins including the first feedthrough pin, the lead port comprises a plurality of electrical contacts including the first electrical contact, and the medical device comprises a plurality of preformed wires including the first preformed, each of the plurality of preformed wires having the proximate portion comprising the number of turns shaped to engage a respective one of the plurality of feedthrough pins and to separate the major portion of the respective preformed wire from the first connector block and the housing when the proximate portion of the respective preformed wire engages the respective one of the plurality of feedthrough pins, the major portion of the respective preformed wire shaped to route the distal portion of the respective preformed wire to a respective one of the plurality of electrical contacts of the header when the proximate portion of the respective preformed wire engages the respective one of the plurality of feedthrough pins.

An example (e.g., "Example 13") of subject matter (e.g., a method) may comprise engaging a first feedthrough pin of a first connector block of a housing of a medical device with a proximate portion of a first preformed wire, the proximate portion comprising a number of turns configured to physically separate a major portion of the first preformed wire from the first connector block and the housing when engaged with the first feedthrough pin, wherein the major portion of the first preformed wire is shaped to route a distal portion of the first preformed wire to a first electrical contact of a lead port of a header when the proximate portion of the first preformed wire engages the first feedthrough pin.

In Example 14, the subject matter of Example 13 may optionally comprise engaging the first electrical contact with the distal portion of the first preformed wire to electrically couple the first feedthrough pin to the first electrical contact using the first preformed wire In Example 15, the subject matter of any one or more of Examples 13-14 may optionally be configured such that the number of turns form a lumen configured to engage the first feedthrough pin.

In Example 16, the subject matter of any one or more of Examples 13-15 may optionally comprise retaining the lumen of the proximate end of the first preformed wire once placed over and pressed onto the first feedthrough pin using a shape of the first feedthrough pin.

In Example 17, the subject matter of any one or more of Examples 13-16 may optionally be configured such that the number of turns comprises at least two turns having different diameters, forming a tapered lumen.

In Example 18, the subject matter of any one or more of Examples 13-17 may optionally be configured such that the number of turns are preformed to include a spacing between at least two successive turns of the number of turns and engaging the first feedthrough pin with the proximate portion of the first preformed wire comprises compressing the spacing between the preformed turns to vary a diameter of at least one of the number of turns.

In Example 19, the subject matter of any one or more of Examples 13-18 may optionally be configured such that the number of turns is between two and four turns, the first feedthrough pin has a length commensurate with the number of turns and a diameter of the preformed wire, and the first preformed wire includes a cobalt or nickel alloy wire.

An example (e.g., "Example 20") of subject matter (e.g., a system) may comprise a housing of a medical device comprising a first connector block, the first connector block comprising a first feedthrough pin, a header comprising a lead port having a first electrical contact, and means for engaging the first feedthrough pin of the first connector block of the housing of the medical device with a proximate portion of a first preformed wire and physically separating a major portion of the first preformed wire from the first connector block and the housing when engaged with the first feedthrough pin, wherein the major portion of the first preformed wire is shaped to route a distal portion of the first preformed wire to the first electrical contact of the lead port of the header when the proximate portion of the first preformed wire engages the first feedthrough pin.

In Example 21, the subject matter of Example 20 may optionally be configured such that the means for engaging the first feedthrough pin of the first connector block of the housing of the medical device with the proximate portion of the first preformed wire and physically separating the major portion of the first preformed wire from the first connector block and the housing when engaged with the first feedthrough pin comprise a number of turns of the proximate portion of the first preformed wire, the number of turns shaped to engage the first feedthrough pin and to physically separate the major portion of the first preformed wire from the first connector block and the housing when the proximate portion of the first preformed wire engages the first feedthrough pin.

In Example 22, subject matter (e.g., a system or apparatus) may optionally combine any portion or combination of any portion of any one or more of Examples 1-21 to comprise "means for" performing any portion of any one or more of the functions or methods of Examples 1-21, or at least one "non-transitory machine-readable medium" including instructions that, when performed by a machine, cause the machine to perform any portion of any one or more of the functions or methods of Examples 1-21.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
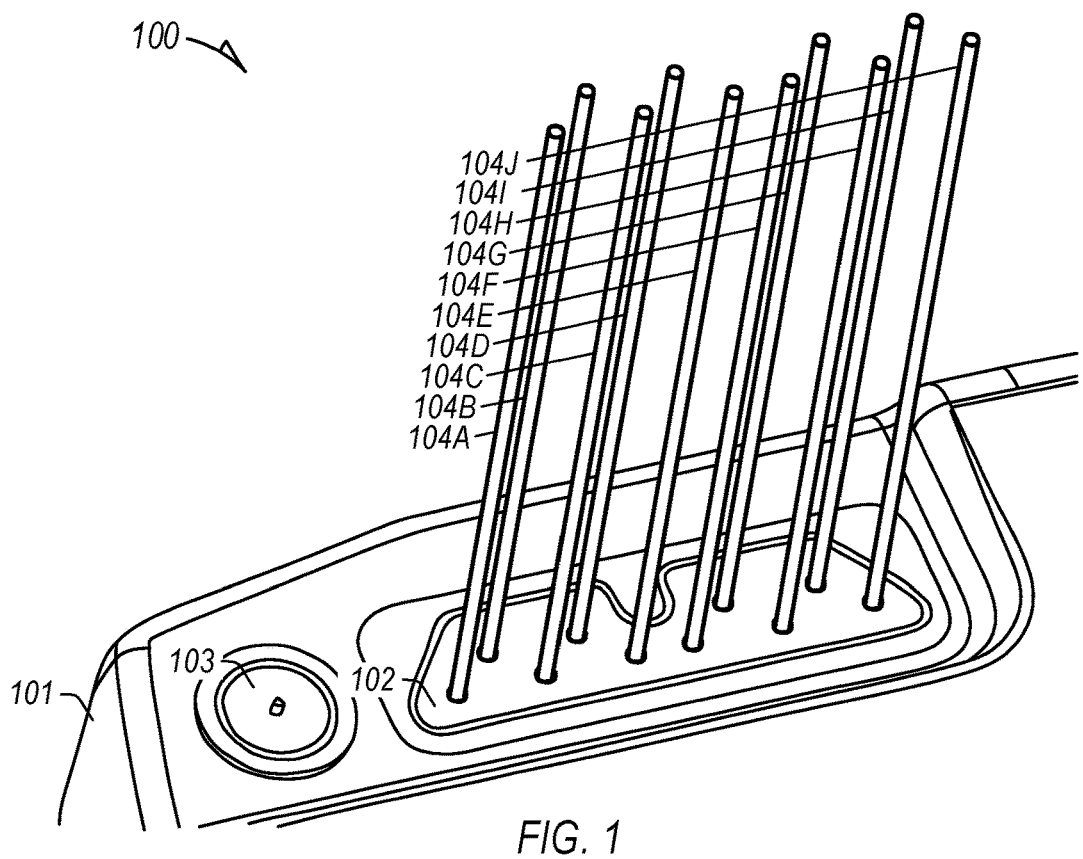
FIG. 1 illustrates an example prior art system comprising portions of an implantable medical device (IMD) including a plurality of extended feedthrough pins.

FIG. 1 illustrates an example prior art system 100 comprising portions of an implantable medical device (IMD) including a housing 101, a first connector block 102, a plurality of extended feedthrough pins 104A-104J, and a second connector block 103. The housing 101 can be composed of a hermetically sealed, biocompatible, electrically-conductive material and can include one or more circuits of the IMD. The first and second connector blocks 102, 103 can be composed of an insulative material (e.g., ceramic, etc.) configured to separate the one or more one or more conductors inside the housing 101 from one or more feedthrough pins, one or more conductors outside the housing 101, and the housing 101 itself.

The IMD can include a header comprising one or more lead ports configured to receive proximate ends of one or more respective leads. The header can be composed of a biocompatible electrically insulative material and can be coupled to a first edge (e.g., a top edge, etc.) of the housing 101 during assembly of the device. The first connector block 102 can be configured to provide electrical communication between one or more conductors or electrical circuits inside the housing 101 to one or more electrical contacts of the header, such as respective electrical contacts of a lead port, etc. The second connector block 103 can be configured to provide electrical communication between one or more conductors or electronic circuits inside the housing 101 to an antenna located outside of the housing 101, such as in the header or one or more other insulative materials outside of the housing 101.

One approach of assembly of the device comprises physically manipulating one or more of the extended feedthrough pins 104A-104J to electrically couple contacts of the first connector block 102, and accordingly to one or more conductors or electrical circuits inside the housing 101, to respective electrical contacts or components of the header.

The length of the feedthrough pins must be long enough to manipulate respective feedthrough pins to corresponding locations of the header. To maintain integrity during manufacture, manipulation, assembly, and use, feedthrough pins are commonly made from platinum group metals (PGMs). The cost of PGMs continue to increase, driving increased cost of IMDs.

In addition, feedthrough pins extending away from the housing 101 can be damaged or bent during handling prior to or during assembly. Accordingly, assembly may require one or more straightening steps prior to or during assembly, increasing assembly cost and complexity. The longer the feedthrough pins, the more likely they are to be damaged or require straightening. Damage to the feedthrough pins can be prevented prior to assembly with a cover, though at additional cost.

Another approach includes using a stamped ribbon to electrically couple contacts of the first connector block 102 to respective electrical contacts or components of the header. However, stamped ribbons can limit design freedom with respect to lead port locations and spacings. In certain examples, stamped ribbons cannot easily navigate routing profiles needed to couple contacts of the first connector block 102 to the header. Further, in certain examples, multiple stamped ribbons may need to be joined together to couple contacts of the first connector block 102 to the header.

The present inventors have recognized, accordingly, that there is a need to reduce the cost or complexity of electrically coupling contacts of the first connector block 102 to respective electrical contacts or components of the header while maintaining or improving performance of such electrical coupling. In an example, a combination of one or more stub feedthrough pins (e.g., relatively short, shorter than the extended feedthrough pins illustrated in FIG. 1) and one or more preformed wires having a number of turns at respective proximate ends of the preformed wires to engage the one or more stub feedthrough pins can be used to replace extended feedthrough pins, such as those illustrated in FIG. 1, at a substantially reduced material and assembly cost.

Preformed wires include wires (e.g., an alloy wire, such as a nickel or cobalt alloy, a nickel-cobalt-chromium-molybdenum alloy (MP35N), a stainless steel alloy, or one or more other alloys, such as a niobium or tantalum alloy wire, etc.) that are pre-shaped, such as using a computer numerical control (CNC) machining tool, prior to assembly, to optimize routing for various medical device housing or header designs or configurations. The wire can be one or more diameters (e.g., 14.5 thou (thousandths of an inch), 15 thou, 12-18 thou, or larger or smaller, depending on the type of medical device, electrical contact, lead port, etc.). In certain examples, the conductors for the preformed wired can cost substantially less than the conductors of the extended feedthrough pins of FIG. 1 (e.g., 80× less, etc.). In an example, the length of the stub feedthrough pins, extending from the first connector block 102, can be commensurate with or slightly longer than the number of turns used by the preformed wire to engage the stub feedthrough pins. For example, if the number of turns at the proximate end of the preformed wire is two to four turns, the length of the stub feedthrough pins can be 3× to 5× the diameter of the preformed wire, etc. In certain examples, a slightly longer stub feedthrough pin, more turns at the proximate end of the preformed wire, or both may be desired, although increasing the width of the header.

A proximate end of the preformed wire can be physically and electrically attached, such as welded (e.g., resistance welded, laser welded, spot welded, etc.) to the one or more respective stub feedthrough pins on the first connector block 102. The preformed wire can be coated prior to attachment, or the wire can be pre-coated prior to machining, such as to prevent exposed conductor risk. In an example, once the proximate end of the preformed wire is connected to the respective stub feedthrough pin on the connector block, the opposite distal end of the preformed wire can be physically and electrically attached, such as welded (e.g., resistance welded, laser welded, spot welded, etc.) to one or more respective electrical contacts of a header. In certain examples, if the wire is coated, laser welding must be used, or the coating can be zoned to allow for spot welding at additional cost.

In certain examples, the preformed wire can have a higher stiffness than the extended feedthrough pins of FIG. 1, providing easier handling and attachment during assembly. Specific preformed wires for each housing/header configuration can reduce the number of discrete conductors extending from the housing. Laser welding of the wires provides for low or zero gap for weld joints, leveraging welding technology of related stent technologies to track wire positions. Coating the preformed wires can prevent exposure of the conductors prior to assembly, and, in certain examples, aid bonding of the preformed wires to the material of the header to promote adhesion. In certain examples, the preformed wires can be laser welded through the coating (e.g., FM generated laser welding).

In an example, the coating can include a colored coating having a contrasting color from the color of the conductive portion of the wire (e.g., a blue, black, or green coating, etc.), or a UV fluorescence additive coating, such as to aid with inspection for damage to one or more of the wire or the coating, or exposed metal on the wire. In certain examples, exposing a UV fluorescence coated wire to UV light can make defects in the wire and coating more apparent, improving assembly procedures and the speed inspection and reducing faults.

Assembly of the medical device using the preformed wires can reduce complexity of wire routing over existing methods, allowing a common low-cost feedthrough for a number of different housing/header configurations, and can remove the need for human visual inspection of exposed conductors during assembly, each reducing system cost and complexity.

Figure 2:
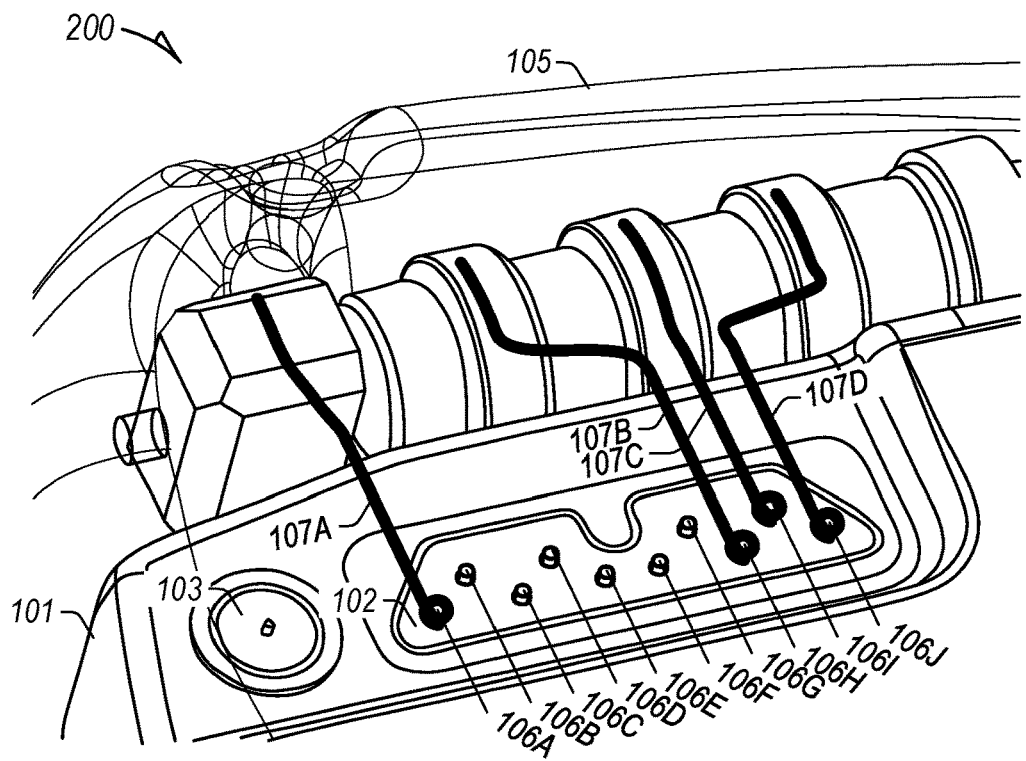
FIG. 2 illustrates an example system comprising portions of an implantable medical device (IMD) including a plurality of stub feedthrough pins and a plurality of preformed wires.

FIG. 2 illustrates an example system 200 comprising portions of an implantable medical device (IMD) including a housing 101 (e.g., a conductive, hermetically-sealed housing (CAN)), a first connector block 102 (e.g., a lead port connector block, etc.), a plurality of stub feedthrough pins 106A-106J, a plurality of preformed wires 107A-107D, a second connector block 103 (e.g., an antenna connector block, etc.), and a header 105 comprising a lead port having a number of electrical contacts.

As above with respect to FIG. 1, the first connector block 102 can be configured to provide electrical communication between one or more conductors or electrical circuits inside the housing 101 to one or more electrical contacts of the header 105, such as respective electrical contacts of the lead port, etc. The second connector block 103 can be configured to provide electrical communication between one or more conductors or electronic circuits inside the housing 101 to an antenna located outside of the housing 101, such as in the header 105.

The plurality of preformed wires 107A-107D are configured to couple electrical contacts of the lead port to respective stub feedthrough pins 106A, 106H, 106I, and 106J of the first connector block 102, as illustrated in FIG. 2. In other examples, the header 105 can include one or more additional lead ports (e.g., two, three, etc.) having the location and number of electrical contacts illustrated in FIG. 2, one or more other configurations with different locations or numbers of electrical contacts, or combinations thereof.

A CNC machining tool can be configured to bend or shape wire to a designed profile in a highly controlled manner at relatively low production and assembly cost, such as in contrast to the extended feedthrough pins of FIG. 1. In addition, the conductive material used for the wire can be an appreciably lower cost material, as a resulting preformed wire does not require variable amounts of bending, straightening, and handling during assembly.

Each of the plurality of preformed wires 107A-107D has a proximate end configured to be attached to a respective one of the plurality of stub feedthrough pins 106A-106J, a distal end configured to be attached to an electrical contact of the header 105, and major portion between the proximate and distal ends. The present inventors have recognized, among other things, that the major portion of the preformed wire can be raised above the housing 101 by the shape of the proximate end.

Figure 3:
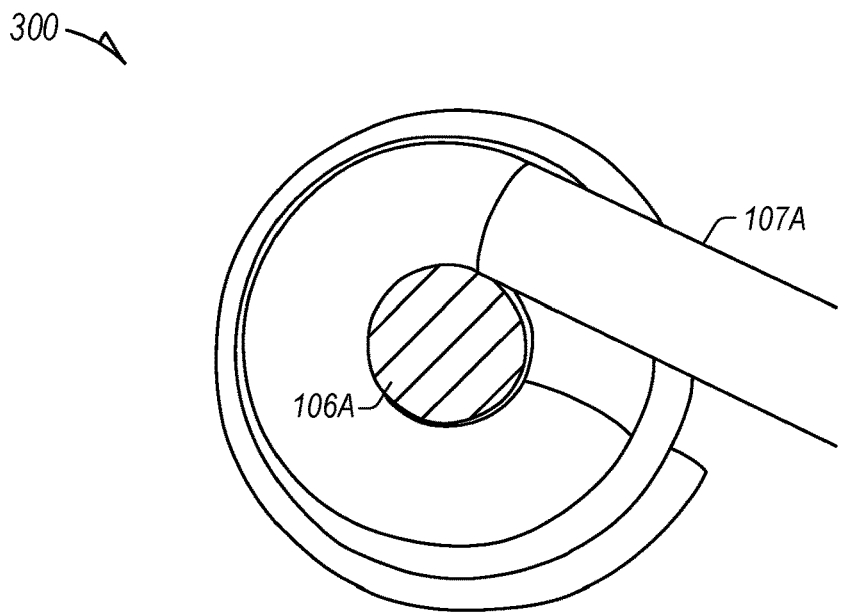
FIGS. 3-6 illustrate example views of a proximate end of a preformed wire and a corresponding stub feedthrough pin.
Figure 4:
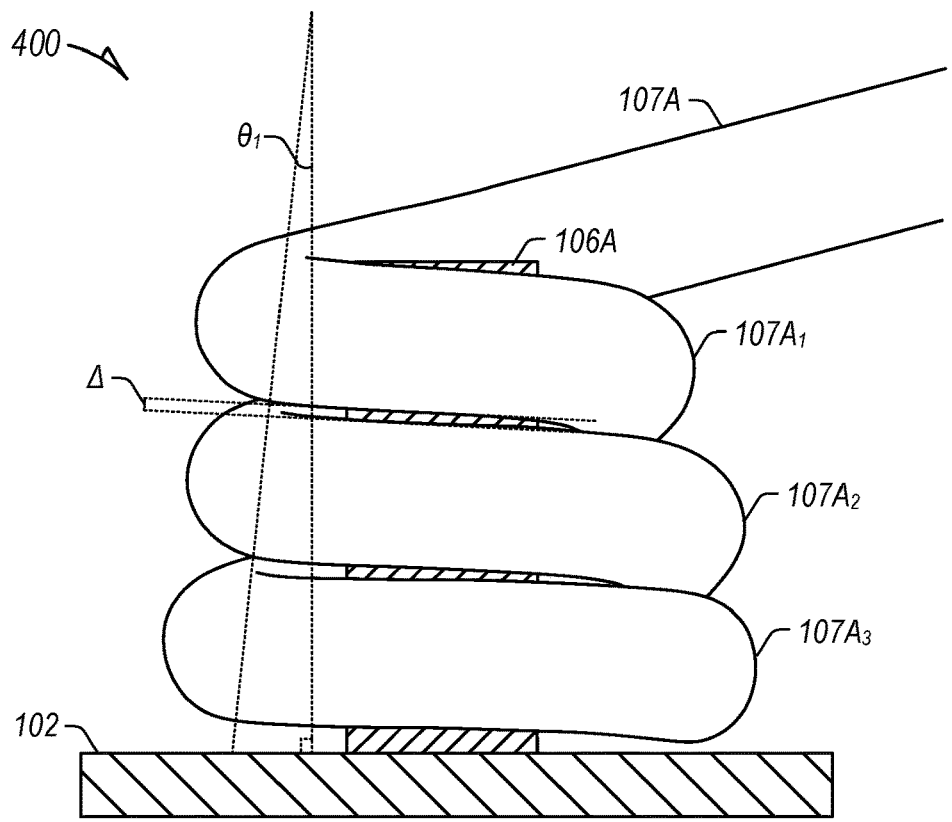

FIGS. 3-4 illustrate example top and lateral views 300, 400 of a proximate end of a first preformed wire 107A and a corresponding stub feedthrough pin 106A. The proximate end of the first preformed wire 107A includes first, second, and third turns $107A_1$, $107A_2$, $107A_3$. In other examples, the proximate end of the preformed wire 107A can include two or more turns (e.g., two, three, four, etc.) configured to raise the preformed wire 107A above a first connector block 102 or a housing, such as that illustrated in FIG. 2. For example, if the preformed wire 107A has a wire diameter of 15 thou and the proximate end has three turns, the proximate end of the preformed wire 107A can be configured to raise a major portion of the preformed wire 107A above the housing by at least 45 thou.

The turns of the proximate end of the first preformed wire 107A can form a lumen that can aid in attaching the first preformed wire 107A to the stub feedthrough pin 106A. During assembly, the lumen can be placed over the stub feedthrough pin 106A and physically attached, such as welded (e.g., resistance welded, laser welded, etc.), proximate the top (e.g., respective to FIGS. 3-4) of the stub feedthrough pin 106A.

In an example, the turns in the first preformed wire 107A can be configured (e.g., bent or shaped) to create a tapered lumen with a smaller diameter at a first opening proximate the first turn $107A_1$ and a larger diameter at a second opening proximate the third turn $107A_3$, such as illustrated by the first angle $\theta_1$ in FIG. 4. The tapered lumen can aid in placement of the proximate end of the preformed wire 107A over the stub feedthrough pin 106A. The larger diameter of the second opening can ease placement of the first preformed wire 107A over the stub feedthrough pin 106A. The smaller diameter of the first opening can improve physical and electrical connection of the first preformed wire 107A to the stub feedthrough pin 106A.

In another example, the distance between the turns, such as illustrated by the distance $\Delta$ in FIG. 4, can be adjusted to alter the height of the major portion of the first preformed wire 107A over the first connector block 102 or the housing, or to provide some variance in one or more of the diameters of the first or second openings of the proximate end of the first preformed wire 107A. For example, pressing the second opening of the proximate end of the first preformed wire 107A against the stub feedthrough pin 106A or an upper surface of the first connector block 102 (e.g., in the configuration illustrated in FIG. 4), compressing the distance Δ between the turns, can increase the diameter of the lumen commensurate with the compression. Releasing the pressure can, in certain examples, return the diameter of the lumen to its previous diameter, or to some diameter therebetween. A larger distance Δ can provide for larger variance in diameter of the lumen, whereas a smaller distance Δ a smaller variance in diameter of the lumen, but more control of the shape and resulting diameter.

In certain examples, the variance described above can be used to aid in placement of the proximate end of the first preformed wire 107A to the stub feedthrough pin 106A, or to enable a compression fit of the smaller diameter of the first opening of the proximate end of the first preformed wire 107A to the stub feedthrough pin 106A. In other examples, the stub feedthrough pin 106A can include one or more other profiles or shapes, and the variance can be used to aid in placement of the proximate end of the first preformed wire 107A over the one or more other profiles or shapes, or to secure the first preformed wire 107A to the stub feedthrough pin 106A.

Figure 5:
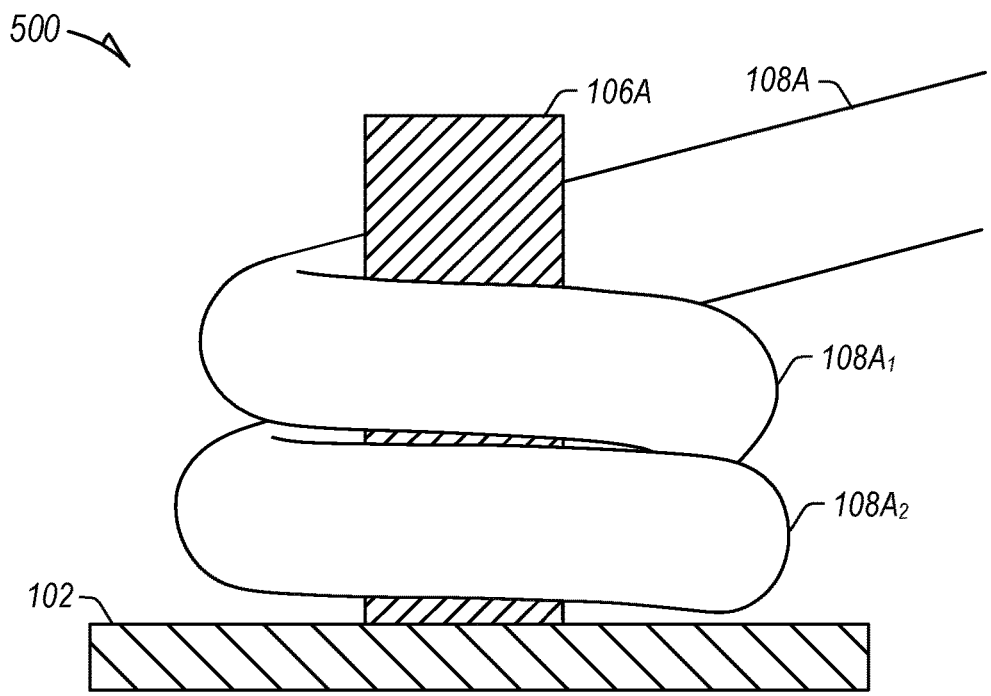

FIG. 5 illustrates an example lateral view 500 of a proximate end of a second preformed wire 108A and a stub feedthrough pin 106A. In contrast to the first preformed wire 107A with three turns of FIGS. 3-4, the proximate end of the second preformed wire 108A of FIG. 5 includes two turns, first and second turns $108A_1$, $108A_2$. In other examples, the proximate end of the second preformed wire 108A can include another number of turns, enough to secure the proximate end of the second preformed wire 108A to the stub feedthrough pin 106A and raise the major portion of the second preformed wire 108A over the first connector block 102 and housing, preventing arching risk with the housing, ferrule, or gold braze bleed down.

The turns can reduce the need for fixturing or component to control height of the second preformed wire 108A above the housing. In certain examples, a single turn may be sufficient to raise the major portion of the second preformed wire 108A over the housing. However, to ensure adequate spacing between conductors, two or more turns may be desired. In an example, once adequate spacing is achieved, additional turns, such as more than four or five turns, can begin to negatively impact the width of the header. Accordingly, in certain examples, the number of turns can include a range between two and four.

Figure 6:
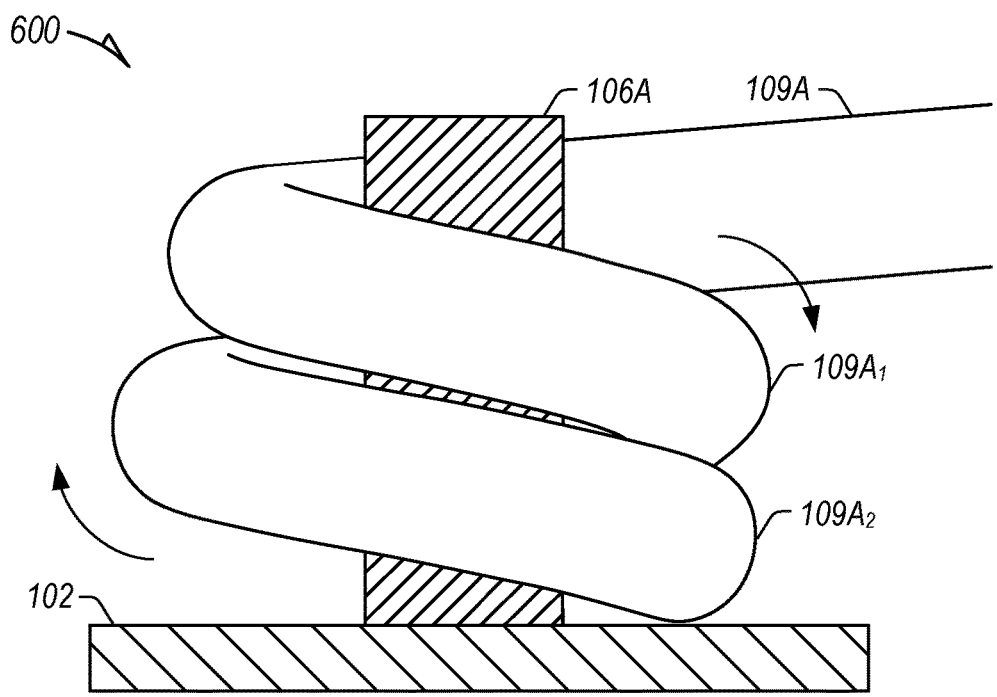

FIG. 6 illustrates an example lateral view 600 of a proximate end of a third preformed wire 109A and a stub feedthrough pin 106A. In contrast to the second preformed wire 108A of FIG. 5, the third preformed wire 109A can be physically rotated to ensure contact with the stub feedthrough pin 106A prior to physical attachment, such as via weld (e.g., resistance weld, laser weld, etc.), etc. In certain examples, the diameter of the lumen of the proximate end of the third preformed wire 109A can be greater than the diameter of the lumen of the second preformed wire 108A of FIG. 5 to provide for such physical rotation.

Figure 7:
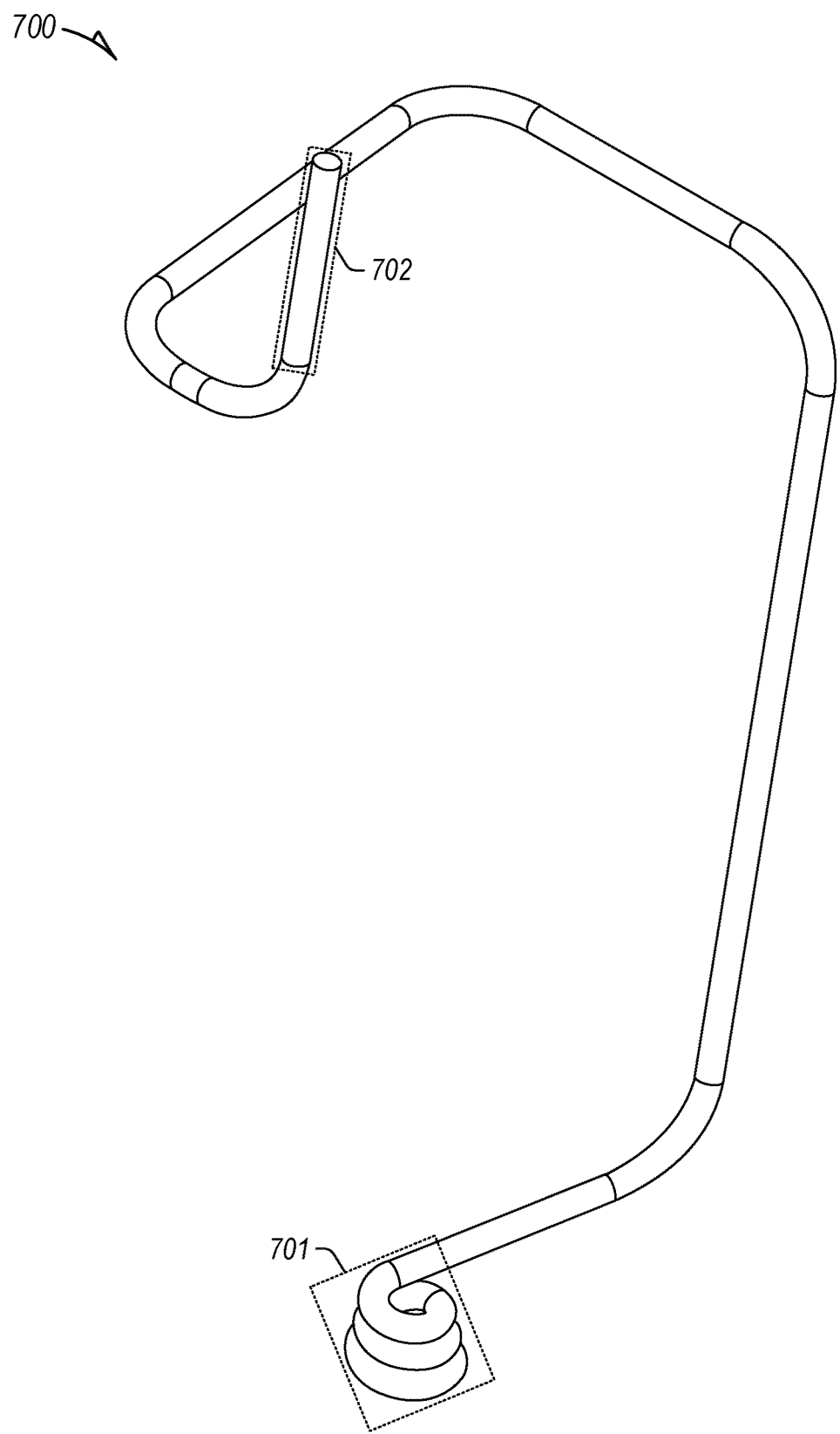
FIG. 7 illustrates an example preformed wire.

FIG. 7 illustrates an example preformed wire 700 including a proximate end 701 having three turns for attachment to a feedthrough pin of a connector block of a housing and a distal end 702 for attachment to an electrical contact of a header. In an example, the remainder of the preformed wire 700 can be considered to be the major portion of the preformed wire 700, shaped for routing between the feedthrough pin of the connector block and the respective electrical contact of the header.

Figure 8:
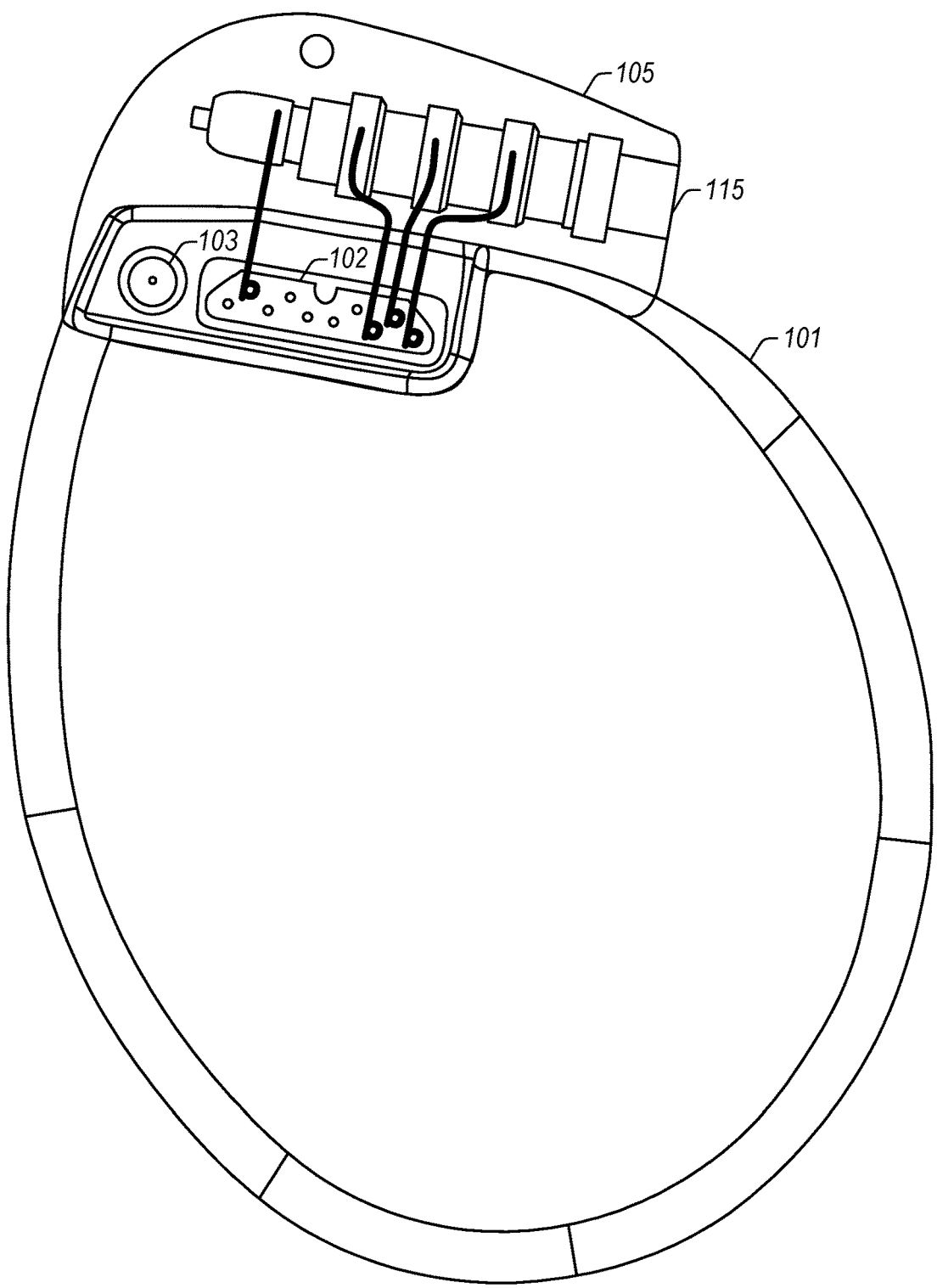
FIG. 8 illustrates an example implantable medical device (IMD) comprising a plurality of stub feedthrough pins and a plurality of preformed wires.

FIG. 8 illustrates an example system 800 comprising an implantable medical device (IMD) including a housing 101, a first connector block 102 comprising a plurality of stub feedthrough pins, a plurality of preformed wires, a secondary connector block 103, and a header 105 comprising a lead port 115 having a number of electrical contacts. The header 105 is configured to cover the first and second connector blocks 102, 103 and any conductors coupled thereto or between the first connector block 102 and one or more electrical contacts of the lead port 115 or other electrical contacts of the header 105.

FIGS. 9-14 illustrate example stub feedthrough pins providing alternate attachment configurations to a respective proximate end of a preformed wire, such as the first preformed wire 107A of FIG. 4.

Figure 9:
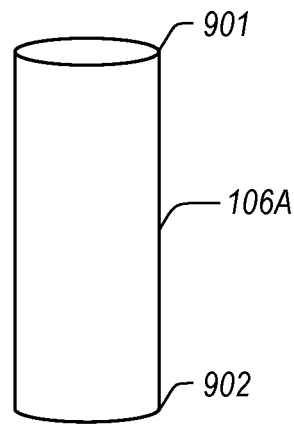
FIGS. 9-14 illustrate example stub feedthrough pins providing alternate attachment configurations to a respective proximate end of a preformed wire.

FIG. 9 illustrates an example first stub feedthrough pin 106A having a top 901 and a bottom 902 with the same or substantially similar diameters, such as illustrated in FIGS. 2-6. In an example, the diameter of the top 901 can be substantially the same as the diameter of a respective top turn of a proximate end of a preformed wire (e.g., the first turn $107A_1$ of the first preformed wire 107A). In other examples, the diameter of the top 901 can be smaller than the diameter of a respective bottom turn of the proximate end of the preformed wire (e.g., the third turn $107A_3$ of the first preformed wire 107A) but the same, substantially similar, or slightly larger (e.g., such that the proximate end of the preformed wire can still be pressed onto the first stub feedthrough pin 106A) than the top turn of the proximate end of the preformed wire.

Figure 10:
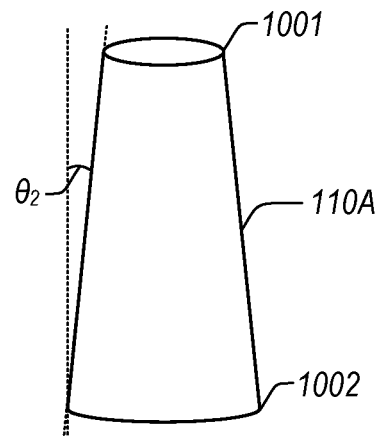

FIG. 10 illustrates an example second stub feedthrough pin 110A having a top 1001 with a smaller diameter than a bottom 1002, creating a profile having a second angle $θ_2$. In one example, the second angle $θ_2$ can correspond to the first angle $θ_1$ from FIG. 4, such that the proximate end of the first preformed wire 107A in FIG. 4 engages the second stub feedthrough pin 110A at each of its turns.

In another example, the second angle $θ_2$ can be steeper than the first angle $θ_1$ from FIG. 4, such that a bottom turn (e.g., the third turn $107A_3$) contacts the second stub feedthrough pin 110A prior to a top turn (e.g., the first turn $107A_1$). Pressing the proximate end of the first preformed wire 107A onto the second stub feedthrough pin 110A after the later turns first contact the second stub feedthrough pin 110A can increase the diameter of the turns until the top turn or all turns contact the second stub feedthrough pin 110A.

In other examples, the second angle $θ_2$ can be more gradual than the first angle $θ_1$ from FIG. 4, such that the top turn (e.g., the first turn $107A_1$) contacts the second stub feedthrough pin 110A prior to the bottom turn (e.g., the third turn $107A_3$). In one example, once the top turn contacts the second stub feedthrough pin 110A, the proximate end of the first preformed wire 107A can be physically attached to the stub feedthrough pin 110A, such as via weld (e.g., resistance weld, laser weld, etc.), etc. In another example, once the top turn contacts the second stub feedthrough pin 110A, the proximate end of the first preformed wire 107A can be pressed onto the second stub feedthrough pin 110A, increasing the diameter of the turns until the bottom turn or all turns also contact the second stub feedthrough pin 110A. Once the top and bottom turns or all turns contact the second stub feedthrough pin 110A, the proximate end of the first preformed wire 107A can be physically attached to the stub feedthrough pin 110A, such as via weld (e.g., resistance weld, laser weld, etc.), etc.

FIGS. 11-14 illustrate example feedthrough pin configurations including engaging means configured to retain a proximate end of a preformed wire once a proximate end of the preformed wire is placed over and pressed onto the feedthrough pins.

Figure 11:
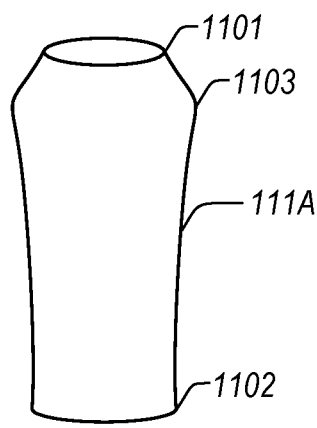

FIG. 11 illustrates an example third stub feedthrough pin 111A having a top 1101 with a smaller diameter (e.g., smaller than the turns of a proximate end of a preformed wire), expanding to an expanded diameter towards an upper section 1103 before again reducing towards a bottom 1102. The smaller diameter of the top 1101 can aid in ease of placement of the proximate end of the preformed wire (e.g., the first preformed wire 107A) over the third stub feedthrough pin 111A. The expanded diameter of the third stub feedthrough pin 111A can be larger than the diameter of a top turn of the preformed wire (e.g., the first turn $107A_1$ of the first preformed wire 107A), such that the proximate end of the preformed wire must be pressed over the expanded diameter of the third stub feedthrough pin 111A, retaining the proximate end on the third stub feedthrough pin 111A. In other examples, the third stub feedthrough pin 111A can include multiple expanded portions between the top and bottom of the third stub feedthrough pin 111A.

Figure 12:
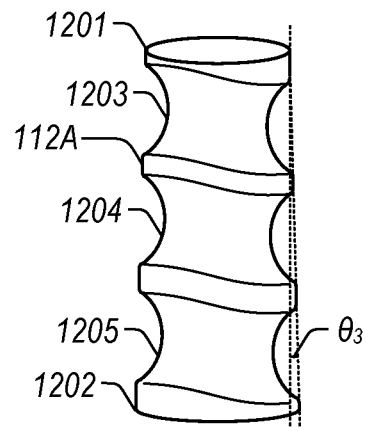

FIG. 12 illustrates an example fourth stub feedthrough pin 112A having first, second, and third indentations 1203, 1204, 1205 between a top 1201 and a bottom 1202, the indentations configured to match the profile of a preformed wire, such as the first preformed wire 107A of FIG. 4. In certain examples, the fourth stub feedthrough pin 112A can have a third angle $\theta_3$, in certain examples corresponding to the first angle $\theta_1$ of the first preformed wire 107A from FIG. 4. In other examples, the third angle $\theta_3$ can be shallower than the first angle $\theta_1$ from FIG. 4, such that when the proximate end of the first preformed wire 107A is placed over the fourth stub feedthrough pin 112A, a top turn (e.g., the first turn $107A_1$) of the first preformed wire 107A contacts the first indentation 1203 of the fourth stub feedthrough pin 112A.

Figure 13:
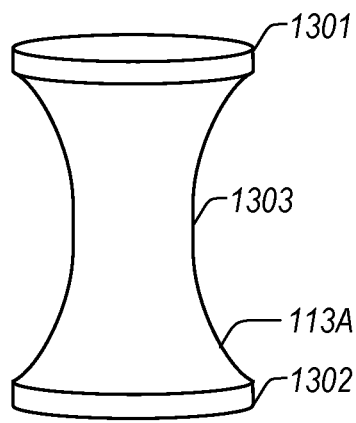

FIG. 13 illustrates an example fifth stub feedthrough pin 113A having a top 1301 and a bottom 1302 having a larger diameter than a center portion 1303. In certain examples, the shape of the fifth stub feedthrough pin 113A can retain a proximate end of a preformed wire (e.g., the first preformed wire 107A) once placed over it, while also separating the proximate end of the preformed wire from a connector block or a housing. In other examples, the top 1301 can include a profile similar to the top 1101 illustrated in FIG. 11, such as to aid initial placement of the proximate end of the preformed wire over the expanded diameter towards the upper section 1103.

Figure 14:
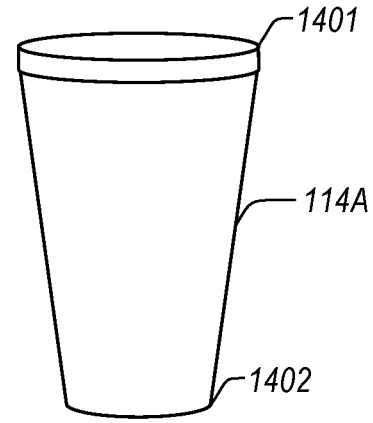

FIG. 14 illustrates an example sixth stub feedthrough pin 114A having a top 1401 having a larger diameter than a bottom 1402. In an example, a top turn of a preformed wire (e.g., the first turn $107A_1$ of the first preformed wire 107A) can have a smaller diameter than the top 1401 of the sixth stub feedthrough pin 114A, such that the shape of the sixth stub feedthrough pin retains the proximate end of the preformed wire once the proximate end is placed over it.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical device, comprising:
   a housing comprising a first connector block on a first surface of the housing, the first connector block comprising a first stub feedthrough pin extending normal from a surface of the first connector block and the first surface of the housing;
   a header comprising a lead port having a first electrical contact; and
   a first preformed wire having a proximate portion, a major portion, and a distal portion,
   wherein the proximate portion of the first preformed wire comprises a number of turns forming a lumen having a depth corresponding to the number of turns, wherein the number of turns that form the lumen is between 2 and 4 turns, wherein each turn has a height corresponding to the diameter of the preformed wire, wherein the number of turns comprises a first turn configured for placement over the first stub feedthrough pin and engagement of a base of the first stub feedthrough pin proximate the surface of the first connector block and a top turn opposite the lumen from the first turn and proximate the major portion of the first preformed wire, wherein the lumen is configured to engage and secure the proximate portion of the first preformed wire to the first stub feedthrough pin and raise the major portion of the first preformed wire over the first connector block and the first surface of the housing,
   wherein the first stub feedthrough pin has a length commensurate with the depth of the lumen, wherein the depth of the lumen is determined by the number of turns of the proximate portion of the first preformed wire, wherein the length of the first stub feedthrough pin is less than 5 diameters of the first preformed wire to not negatively impact the width of the header,
   wherein the major portion of the first preformed wire is pre-shaped prior to assembly to optimize routing the first preformed wire between the first stub feedthrough pin and the first electrical contact of the lead port of the header.

2. The medical device of claim 1, wherein the first preformed wire is configured to electrically couple the first stub feedthrough pin to the first electrical contact when the proximate portion of the first preformed wire is engaged with and around the first stub feedthrough pin and the distal portion of the first preformed wire is coupled to the first electrical contact,
   wherein the first preformed wire has a diameter between 12 and 18 thousands of an inch,
   wherein the first stub feedthrough pin has a diameter larger than the diameter of the first preformed wire,
   wherein the first turn, when engaged with the first stub feedthrough pin, is proximate the first surface of the first connector block.

3. The medical device of claim 1, wherein the plurality of turns of the proximate portion of the first preformed wire form a pre-shaped lumen, prior to placement over the first stub feedthrough, the pre-shaped lumen configured to engage the first stub feedthrough pin and raise the major portion of the first preformed wire over the first connector block and the first surface of the housing.

4. The medical device of claim 3, wherein the first stub feedthrough pin comprises a non-uniform profile shaped to retain the lumen of the proximate end of the first preformed wire once placed over and pressed onto the first stub feedthrough pin.

5. The medical device of claim 4, wherein the first stub feedthrough pin includes engaging means configured to retain the proximate end of the first preformed wire once the lumen is inserted over and pressed onto the first stub feedthrough pin.

6. The medical device of claim 3, wherein the plurality of turns comprises between two and four turns, the plurality of turns having different diameters, forming a tapered lumen to be placed over and engage the first stub feedthrough pin.

7. The medical device of claim 6, wherein the top turn is adjacent to the major portion of the first preformed wire having a diameter of a corresponding portion of the lumen smaller than that of the first turn, wherein the first turn is a bottom turn adjacent a proximate end of the proximate portion of the first preformed wire,
wherein the diameter of the bottom turn of a corresponding portion of the lumen larger than the top turn aids placement of the proximate portion of the first preformed wire over and around the first stub feedthrough pin and the diameter of the top turn smaller than the bottom turn aids engagement of the proximate portion of the first preformed wire with and around the first stub feedthrough pin.

8. The medical device of claim 1, wherein the plurality of turns are positioned to include a spacing between at least two successive turns of the plurality of turns, the spacing configured to provide variance of a diameter of at least one of the plurality of turns when compressed.

9. The medical device of claim 1, wherein the first preformed wire includes an alloy wire having a coating that contrasts a physical appearance of the alloy wire to aid in visual inspection of the first preformed wire, and
wherein the coating includes at least one of a colored or UV fluorescence coating.

10. The medical device of claim 1, wherein the first connector block comprises a plurality of stub feedthrough pins including the first stub feedthrough pin,
wherein the lead port comprises a plurality of electrical contacts including the first electrical contact, and
wherein the medical device comprises a plurality of preformed wires including the first preformed wire, each of the plurality of preformed wires having the proximate portion comprising the plurality of turns shaped to wrap around and engage a respective one of the plurality of stub feedthrough pins and to separate the major portion of the respective plurality of preformed wires above the surface of the first connector block and the first surface of the housing when the proximate portion of the respective preformed wire is engaged with and around the respective one of the plurality of stub feedthrough pins, the major portion of the respective preformed wire shaped to route the distal portion of the respective plurality of preformed wires to a respective one of the plurality of electrical contacts of the header when the proximate portion of the respective preformed wire is engaged with and around the respective one of the plurality of stub feedthrough pins.

11. The system of claim 1, wherein the first connector block is located on a side portion of the housing, and
wherein the header is located on a top portion of the housing.

12. The system of claim 1, wherein the first stub feedthrough pin has a length between 3 and 5 times larger than the diameter of the first preformed wire.

13. A method, comprising:
engaging a first stub feedthrough pin extending normal from a surface of a first connector block on a first surface of a housing of a medical device with a lumen of a proximate portion of a first preformed wire formed from a number of turns of the proximate portion of the first preformed wire, wherein the number of turns that form the lumen is between 2 and 4 turns, wherein each turn has a height corresponding to the diameter of the preformed wire, wherein the number of turns comprises a first turn configured for placement over the first stub feedthrough pin and engagement with a base of the first stub feedthrough pin proximate the surface of the first connector block and a top turn opposite the lumen from the first turn and proximate a major portion of the first preformed wire, wherein the lumen is configured to engage and secure the proximate portion of the first preformed wire to the first stub feedthrough pin and raise the major portion of the first preformed wire over the first connector block and the first surface of the housing,
wherein the first stub feedthrough pin has a length commensurate with the depth of the lumen, wherein the depth of the lumen is determined by the number of turns of the proximate portion of the first preformed wire, wherein the length of the first stub feedthrough pin is less than 5 diameters of the first preformed wire to not negatively impact the width of the header,
wherein the major portion of the first preformed wire is pre-shaped prior to assembly to optimize routing the first preformed wire between the first stub feedthrough pin and the first electrical contact of the lead port of the header.

14. The method of claim 13, comprising:
engaging the first electrical contact with the distal portion of the first preformed wire to electrically couple the first stub feedthrough pin to the first electrical contact using the first preformed wire,
wherein the first preformed wire has a diameter between 12 and 18 thousands of an inch,
wherein the first stub feedthrough pin has a diameter larger than the diameter of the first preformed wire,
wherein the first turn, when engaged with the first stub feedthrough pin, is proximate the first surface of the first connector block.

15. The method of claim 13, wherein the plurality of turns of the proximate portion of the first preformed wire form a pre-shaped lumen, prior to placement over the first stub feedthrough, the pre-shaped lumen configured to engage the first stub feedthrough pin and raise the major portion of the first preformed wire over the first connector block and the first surface of the housing,
wherein the first stub feedthrough pin comprises a non-uniform profile, and wherein the method includes:
retaining the lumen of the proximate end of the first preformed wire once placed over and pressed onto the first stub feedthrough pin using the non-uniform profile of the first stub feedthrough pin.

16. The method of claim 13, wherein the first connector block is located on a side portion of the housing, and wherein the header is located on a top portion of the housing.

\* \* \* \* \*